United States Patent [19]
Smyth

[11] 3,939,843
[45] Feb. 24, 1976

[54] TRANSVENOUS ELECTRODE
[75] Inventor: Nicholas P. D. Smyth, Bethesda, Md.
[73] Assignee: Medtronic, Inc., Minneapolis, Minn.
[22] Filed: Mar. 4, 1974
[21] Appl. No.: 447,552

[52] U.S. Cl. .............................. 128/404; 128/419 P
[51] Int. Cl.² ............................................ A61N 1/04
[58] Field of Search ........ 128/404, 418, 419 P, 407, 128/408, 2.05 F

[56] References Cited
UNITED STATES PATENTS

| | | | |
|---|---|---|---|
| 3,487,826 | 1/1970 | Barefoot | 128/2.05 F |
| 3,516,412 | 6/1970 | Ackerman | 128/418 |
| 3,729,008 | 4/1973 | Berkovits | 128/418 |
| 3,754,555 | 8/1973 | Schmitt | 128/418 |

FOREIGN PATENTS OR APPLICATIONS
246,004  11/1969  U.S.S.R. ........... 128/419 P

OTHER PUBLICATIONS
Dodinot et al., Annals of N.Y. Academy of Sciences Vol. 167, Art. 2, Oct. 30, 1969, pp. 1038–1043.

Primary Examiner—William E. Kamm
Attorney, Agent, or Firm—Lew Schwartz; Wayne A. Sivertson

[57] ABSTRACT

A transvenous lead including a conductor encased in an insulating material which is generally inert in body fluids and tissues, the conductor being connected to an exposed, electrically conductive electrode at, or adjacent to, the lead terminus. At least one tine extends from the casing adjacent the lead terminus for engaging the inner wall or trabeculae of an internal body organ or chamber to urge the electrode in a given generally transverse direction, all of such tines extending from the casing in directions which fall within an 180° arc around its periphery with no tine extending in a direction less than 90° from the given direction. In one preferred embodiment, the electrode forms a conductive lead tip and includes a portion skewed toward the given direction.

23 Claims, 9 Drawing Figures

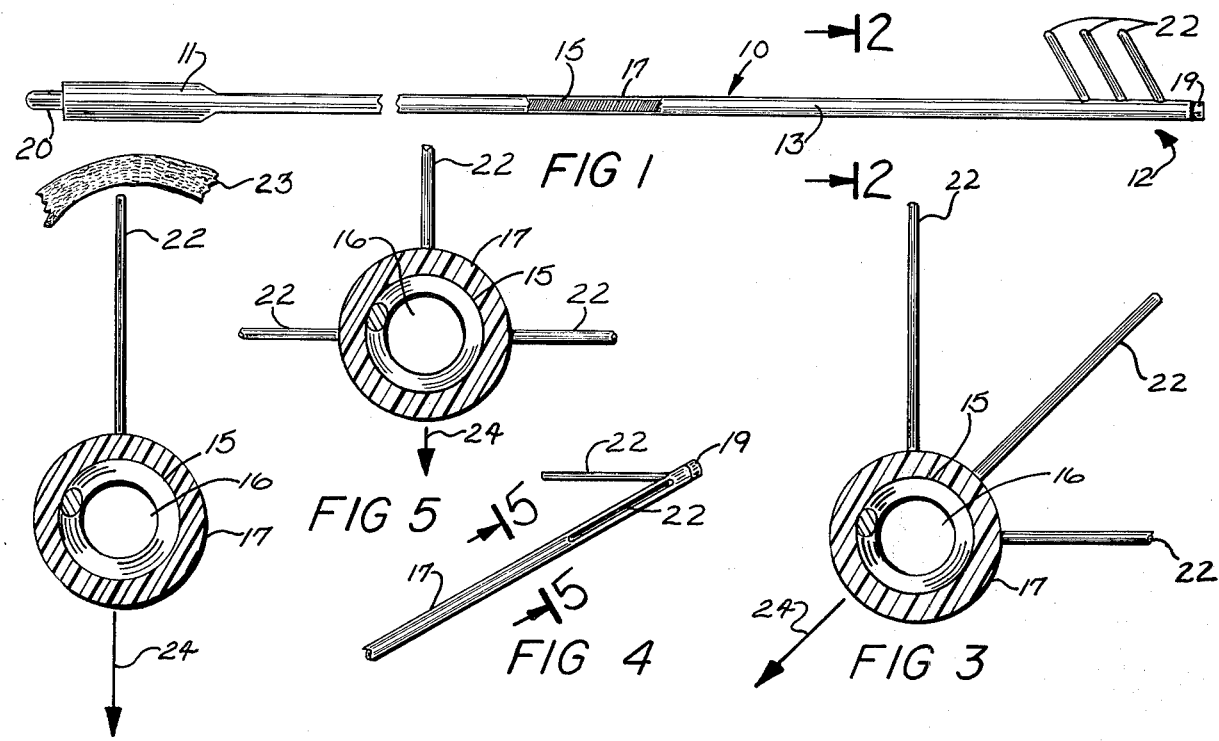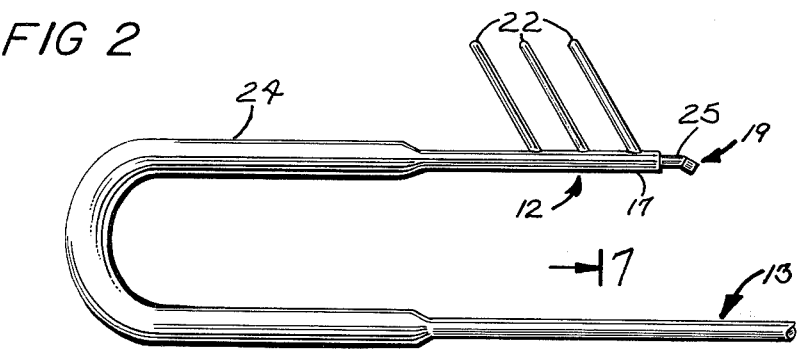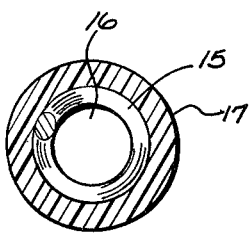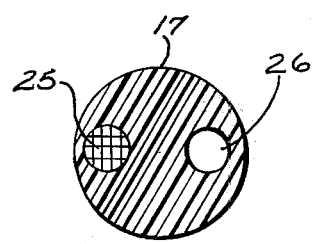

TRANSVENOUS ELECTRODE

BACKGROUND OF THE INVENTION

Electrical contact with various portions of the body through a transvenous approach has found increasing interest in recent years. Of particular interest is a reliable endocardial electrical contact with the atrium. Such a contact allows atrial pacing or atrial synchronized pacing without a thoracotomy thereby preserving the contribution of atrial contraction in the overall cardiac output while significantly lowering patient risk and morbidity. Additionally, an atrial contact would be advantageously employed for arrhythmia management and other purposes which may not be accomplished through ventricular electrical stimulation. For reasons well known to those skilled in the art, the greatest advantages from an electrical contact with the heart can be obtained by contacting the right atrium, the right atrial appendage providing a suitable site.

In the U.S. Pat. application Ser. No. 372,269, of Paul Citron and Eugene A. Dickhudt, filed June 21, 1973, now U.S. Pat. No. 3,902,501 and commonly owned with the present application and incorporated herein by reference, there are discussed several prior attempts to accomplish an endocardial electrical contact with the atrium. Part of that discussion centers upon a paper co-authored by me which described a J-shaped catheter with a flange near the tip. The catheter was inserted into the right atrium through a transvenous approach after being straightened by the insertion of a stylet. The catheter assumed its preformed J-shape within the atrium to facilitate placement of the electrode tip in the artrial appendage when the stylet was withdrawn. The atrial trabeculae and shape of the catheter were relied upon to maintain the lead in location until the heart tissue itself enveloped and fixed the tip.

A sensing atrial endocardial electrode is also described in the referenced patent application. This prior art electrode employed a J-shaped applicator catheter which was used to direct the electrode tip into the right atrial appendage. The lead was provided with two fine wire hooks positioned at its tip each ending in a relieving loop. The hooks were held back by the applicator catheter to spring out and anchor the electrode in the trabeculae of the right atrial appendage when the electrode tip left the end of the applicator catheter.

The deficiencies in the prior art techniques described above are detailed in the referenced patent application which provides a novel electrode uniquely adapted for use as an atrial endocardial electrode. In essential part, the lead of the referenced patent application, as shown in FIG. 1 thereof, is comprised of a body member terminating at an exposed electrically conductive tip having a plurality of tines extending at an acute angle from the body member from a position adjacent the tip. As so constituted, the tines will become involved with the cooperating trabeculae of the right atrial appendage to push against them and maintain the tip in electrical contact with the inner wall of the right atrial appendage. For this purpose, it is contemplated that the tines extend generally around the circumference of the body member with the number of tines not being critical to the operativeness of the invention. The tines of the referenced patent application are intended to push against the coperating trabeculae to urge the lead in a direction defined generally by its longitudinal axis. This, the tines of the referenced patent application are effective to urge only the terminus or tip of its lead into electrical contact with the inner wall of the atrial appendage, or similar organs or chambers.

BRIEF SUMMARY OF THE PRESENT INVENTION

The present invention provides a transvenous lead including a conductor encased in an insulating material which is generally inert in body fluids and tissues, the conductor terminating at an exposed electrically conductive electrode at, or adjacent to, the lead terminus. At least one tine extends from the casing adjacent the lead terminus for engaging the inner wall or trabeculae of an internal body organ or chamber to urge the electrode in a given, nominally transverse, direction. Through this transverse urging, the lead of the present invention may be employed in any body organ or chamber to urge the electrode against the organ or chamber side wall through the engagement of the tines with such trabeculae as might exist and/or the opposing sidewall of the organ or chamber. Also, the electrode may be positioned at any point along the lead that is within the influence of the tines. Thus, the lead of the present invention has a wider application than that of the referenced patent application. Also, in the particular environment of the referenced application, namely the right atrial appendage, it has been found that a lead constructed according to the present invention is easier to position and provides at least as reliable electrical contact with no indication of any deficiencies in its securement.

The many advantages of the present invention are provided by configuring the tines of the referenced patent application such that all of the tines extend from the casing in directions which fall within a 180° arc around the casing periphery. In this way, the tines cooperate to urge the electrically conductive electrode in a given, nominally transverse, direction and no tine extends in a direction less than 90° from the given direction. In a preferred embodiment, the electrode comprises a conductive tip including a portion skewed from the longitudinal direction of the conductor towards the given direction.

The many objects, advantages and novel features of the present invention will become apparent from the following detailed description of the invention when considered in conjunction with the accompanying drawings.

BRIEF DESCRIPTION OF THE DRAWINGS

FIG. 1 shows a preferred embodiment of the present invention.

FIG. 2 shows a cross section of the preferred embodiment of FIG. 1 taken along the Line 2—2 in FIG. 1.

FIG. 3 shows a modification of the embodiment of FIG. 1 as viewed along the Line 2—2 in FIG. 1.

FIG. 4 shows another preferred embodiment of the present invention.

FIG. 5 shows a cross section of the preferred embodiment of FIG. 4 taken along the Line 5—5 in FIG. 4.

FIG. 6 shows an additional preferred embodiment of the present invention.

FIG. 7 shows a cross section of the preferred embodiment of FIG. 6 taken along the Line 7—7 in FIG. 6.

FIG. 8 shows a modification to the preferred embodiment of FIG. 7.

DETAILED DESCRIPTION OF THE DRAWINGS

Figure 9:
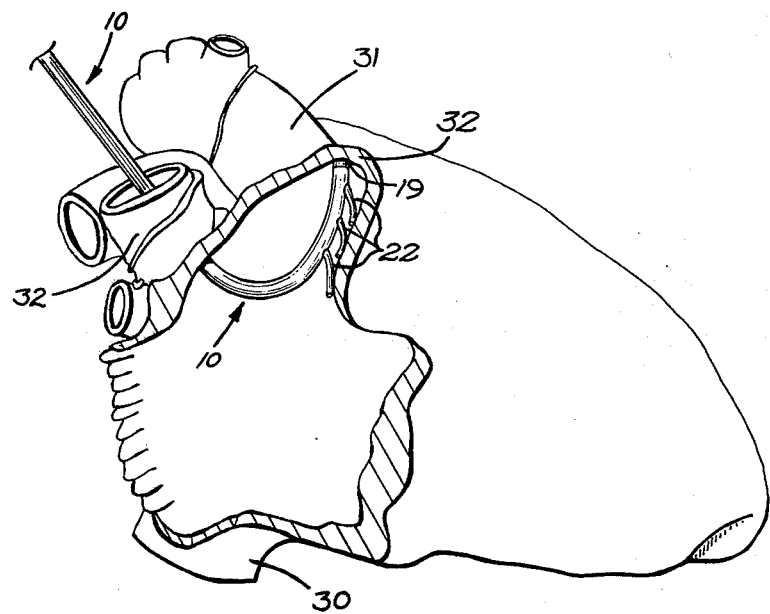
FIG. 9 shows a partial cutaway of the heart with an embodiment of the present invention in position therein.

FIG. 1, which illustrates a preferred embodiment of the present invention, shows a lead 10 having a connector portion 11, electrode protion 12 and central portion 13. The cross section of the central portion 13 may be as illustrated in FIG. 7. That is, an electrical conductor formed of a coiled member 15 having a void lumen 16 is encased in an insulating material 17 which is generally inert in body fluids and tissues, for example, silicone rubber or polyurethane. The conductor 15 is in electrical contact with a conductive tip 19 and extends from the conductive tip 19 through the central portion 13 and the connecting portion 11 and into electrical contact with a connecting pin 20. The connecting pin 20 is adapted for connection with a remote electrical device in known manner and has a lumen therethrough coincident with the lumen 16 of the conductor 15. With this configuration, it is possible to insert a stylet through the end of the connecting pin 20, through the lumen 16 of conductor 15 into abutment with the conducting tip 19. The electrically conductive tip 19 may be of any material suitable for the environment, platinum-iridium, for example. Also, although the conductive tip 19 is a preferred electrode embodiment, any electrode within the electrode portion 12 may be employed.

Extending from the casing material 17 from locations adjacent the conductive tip 19 are a plurality of tines 22. The tines 22 are of a pliant material which is generally inert to body fluids and tissues, silicone rubber or polyurethane, for example, and may be attached to the electrode portion 12 of the lead 10 in any convenient manner. For example, they may be molded so as to be unitary with the electrode portion 12. Alternatively, the tines 22 may extend from a ring which surrounds the electrode portion 12 and is adhered thereto in any convenient manner. The tines 22 are shown making an acute angle with the longitudinal axis of the lead 10. As will be fully appreciated from the following description, the angle of inclination of the tines 22 with respect to the longitudinal axis is not critical and may have any convenient value consistent with their purpose to cooperate with body tissues to maintain the tip 19 in electrical contact.

Referring now to FIG. 2, there is shown a cross-sectional view of the embodiment of FIG. 1 taken along the line 2—2. From FIG. 2, it is apparent that the tines 22 of FIG. 1 extend in the same general direction from different locations on the casing material 17. Inasmuch as the direction of the tines with respect to the longitudinal axis is not critical, the term 'direction' as employed herein and in the claims is intended to mean a direction within a plane transverse to the longitudinal axis of the electrode 10. For example, although the tines may extend in a direction which has a component along the longitudinal axis of the electrode, the term 'tine direction', unless specifically stated otherwise, shall mean the component of tine direction which is transverse to the longitudinal axis of the lead 10.

It is apparent from FIG. 2, that if the tines 22 are brought into contact with a surface oriented such as that designated by reference numeral 23 which may be the inner surface of a body organ or chamber, the tines would tend to urge the electrode portion 12 of the lead in the transverse direction indicated by the arrow 24. Thus, the tines oriented as illustrated in FIG. 2 can be said to have a tendency to urge the lead in a given, nominally transverse, direction, that direction being the direction indicated by the arrow 24. Of course, depending upon the orientation of the body tissues with which the tines 22 cooperate, and the form of that cooperation, the actual direction may differ from the given nominal direction. In any event, the transverse component of the direction in which the tines 22 actually urge the lead 10 will sufficiently approximate the given direction 24 so that a lead constructed within the constraints detailed below will be operative.

Referring now to FIG. 3, there is shown a modification of the preferred embodiment of FIG. 2 as seen in cross section taken along the Line 2—2 of FIG. 1. In this embodiment, the tines 22 are shown spaced partially around the periphery of the casing material 17. The tines may be within the same transverse plane or spaced along the longitudinal axis as in the embodiment of FIG. 1. In either case, the transverse component of the direction in which the tines will tend to urge the lead is again shown at 24. An additional preferred embodiment is illustrated in FIGS. 4 and 5. Here, the tines 22 again extend at acute angles with respect to the longitudinal axis. The transverse components of their direction of extension all lie within an arc of 180° around the periphery of the casing material 17. Again, the transverse component of the direction in which the tines 22 urge the lead 10 is indicated at 24 and none of the tines extend from the casing material 17 in a direction less than 90° from the given direction 24. Indeed, the embodiments of FIGS. 2 and 3 similarly fall within the same constraints and, from FIGS. 2-5 it can be seen that tines configured within those constraints will tend to urge the lead 10 in the direction 24 without impeding that motion to result in contact of the electrode 19 with the inner wall of a body organ or chamber. Again, the constraints can be alternatively phrased: all of the tines 22 must extend from the casing 17 in directions which fall within no more than an 180° arc around the periphery of the casing; or none of the tines must extend in the direction whose transverse component is less than 90° from the direction indicated at 24. Also, it should be noted that in the embodiments of FIGS. 1 – 5 the tines are generally symmetrically arranged with respect to the direction 24 although it is possible to arrange them otherwise within the contrraints given above while still maintaining the operativeness of the invention.

Referring no to FIG. 6, there is shown another preferred embodiment of the present invention. In this embodiment, the tines 22 are configured as illustrated in FIGS. 1 and 2 although other tine configurations within the stated constraints may be employed. As shown in FIG. 6, the lead of this embodiment has a preformed J member 24 intermediate the central portion 13 and electrode portion 12. The central portion 13 may run to a connector portion 11 such as that illustrated in FIG. 1.

The preformed J member 24 is intended to adapt the lead of the present invention for use in the right atrial appendage. A stylet is threaded through the lumen 16 of the electrical conductor 15 to straighten the J member 24. As straightened, the lead is inserted through a blood vessel in known fashion. When the electrode portion 12 and J member 24 reach the atrium, the stylet is removed and the lead assumes the J configuration illustrated in FIG. 6. In this configuration, the electrode portion 12 is easily inserted into the atrial appendage with the tines 22 cooperating with the atrial trabeculae to urge the conductive tip 25 into contact with the appendage wall. To facilitate the electrical contact with the appendage wall, the conductive tip 19 is shown with a portion 25 which is skewed from the longitudinal axis of the electrode portion towards the direction indicated as 24 in FIG. 2. The tip 19 need not be skewed, it being necessary only that the tip extend, in the direction 24 of FIG. 2, at least to or past the casing material 17 which forms the electrode portion 12. The skewed portion 25 is a preferred form of accomplishing the extension.

The J member 24 may be formed as described in the article I co-authored, which article is discussed and identified in the referenced application. Alternatively, the J portion may be formed in the manner described in U.S. Pat. No. 3,729,008, issued Apr. 24, 1973, to Barough V. Berkovitis. In either case, the J member 24 has a cross-sectional area greater than that of either the central portion 13 or electrode portion 12. This greater cross-sectional area in the J member 24 adds rigidity to that member and tends to overcome the tendency of the coil 15 to straighten as well as having a greater ability to overcome the effects of gravity on the lead. Of course, any other techniques for preforming the J member 24 may be employed whether or not it results in a J member having a greater cross-sectional area than either the electrode portion 12 or the central portion 13. Alternatively, the J applicator catheter technique described in the referenced application may be employed to position the lead of the present invention within the right atrial appendage thereby eliminating any need to preform a J member within the lead itself.

FIG. 9 is a partial cutaway of the heart showing the lead and tip electrode of the present invention in a position within the right atrial appendage. For reference, 30 is the inferior vena cava, 31 is the aorta and 32 is the superior vena cava. The electrode of the present invention 10 is shown entering the right atrium through the superior vena cava. Within the right atrium, the electrode 10 angles and its tip is within the right atrial appendage 32. As shown, the tines 22 engage the side wall of the appendage and urge the tip 19 into engagement with the opposing sidewall. FIG. 9 is intended only to illustrate the lead of the present invention in one operative position. Other positions and tine configurations may be employed and the lead may be placed in other body organs or chambers. Within the environment of FIG. 9, the lead may be configured as shown in FIGS. 1 or 6, and placed in position in any known manner.

Referring now to FIGS. 7 and 8, there are shown alternative conductor embodiments which may be employed in any of the embodiments of FIGS. 1, 4 or 6. In FIG. 7, there is shown a coiled conductor 15 having an internal lumen 16, the coil 15 being encased by an insulating material 17. This embodiment had been discussed with reference to FIG. 1. FIG. 8 shows a multistrand wire 25 which may be of platinum, for example, and is commonly referred to as "tinsel wire". With this type of conductor and assuming a preformed J configuration, it is necessary to provide a stylet lumen as at 26 to straighten the J member 24. The wire 25 and lumen 26 are surrounded by an insulating material 17 which may be identical to that in the embodiments of FIGS. 2 and 7. In the embodiment of FIG. 8, the conductor 25 and lumen 26 are shown spaced off of the longitudinal axis of the insulating material 17. Alternatively, the conductor 25 may be positioned along the longitudinal axis with the stylet lumen 26 spaced therefrom. Further, in both the embodiments of FIGS. 7 and 8 the lumens 16 and 26 may be lined with Teflon or any other appropriate material to facilitate the insertion and removal of the stylet.

From the above, it can be seen that the present invention provides an improved medical lead uniquely adapted to make electrical contact with the inner wall of an internal body organ or chamber through a transvenous approach. The lead provides means for cooperating with body tissue to urge the electrode portion of the lead and an electrode carried by the electrode portion into contact with the organ or chamber wall. In one embodiment, the lead is provided with a preformed J-shaped member which adapts the lead advantageously for use in the atrial appendage. In this and other forms, the lead may be employed in any appropriate internal organ or chamber. The tines are dimensioned according to the application and are of a pliant material which is sufficiently rigid to accomplish their purpose without having a tendency to damage tissue while being sufficiently pliable so that they may be disengaged if necessary.

Obviously, many modifications and variations of the present invention are possible in light of the above teachings. An example of such a modification would be to make all or a portion of the lead 10 or the tines 22, or both, radiopaque to facilitate the positioning by observation through X-ray, fluoroscopy, etc. This can be accomplished through impregnation with carbon, barium sulfate, or Tantalum. Of course, any suitable substance and method will be acceptable for this purpose. Also, since the tines have the ability to urge the entire electrode portion 12 into contact with the side wall of a body organ chamber or organ, the electrode may be positioned at any point within the electrode portion. Alternatively, the lead may be provided with a tip electrode as well as a second electrode spaced from the tip to operate in a bipolar mode. It is therefore to be understood that, within the scope of the appended claims, the invention may be practiced otherwise than as specifically described.

What is claimed is:

1. In a transvenous electrode carrying lead of the type having an electrical conductor encased in a material which is generally inert to body fluids and tissue and having body tissue engaging means of a material which is generally inert to body fluids and tissue extending from the casing at a location adjacent to the lead terminus, the improvement wherein said body tissue engaging means comprises a plurality of non-conducting tine means extending from said casing material in directions which fall within no more than a 180° arc around the periphery of said casing material for urging the electrode carrying portion of lead in a transverse direction outside of said 180° arc, said tine means being entirely of a pliant material having sufficient rigidity to cooperate with body tissue and effect said urging while being sufficiently pliant to prevent penetration of said body tissue.

2. The transvenous lead of claim 1 wherein said tine means each extend in a direction generally opposed to said transverse direction from different locations on said casing material.

3. The transvenous lead of claim 2 wherein said electrode is at the terminus of said lead, said electrode comprising a conductive tip having a skewed portion extending from said casing material generally in said transverse direction.

4. The transvenous lead of claim 1 wherein said electrode is at the terminus of said lead, said electrode comprising a conductive tip having a skewed portion extending beyond said casing material in a direction having a transverse component outside said 180° arc.

5. The transvenous lead of claim 4 wherein said tine means are generally symmetrically arranged with respect to said transverse direction.

6. The transvenous lead of claim 1 wherein said casing means has a preformed J configuration and a lumen adapted to accept a stylet.

7. The transvenous lead of claim 6 wherein the portion of said casing means which forms said J configuration has a larger cross-sectional area than the remainder of said casing means.

8. The transvenous lead of claim 7 wherein said electrode is at the terminus of said lead, said electrode comprising a conductive tip having a skewed portion extending beyond said casing material in a direction having a transverse component outside said 180° arc.

9. The transvenous lead of claim 8 wherein said tine means are generally symmetrically arranged with respect to said transverse direction.

10. The transvenous lead of claim 9 wherein said tine means each extend in a direction generally opposed to said transverse direction from different locations on said casing means.

11. A body implantable lead adapted to make electrical contact with the inner wall of an internal body organ or chamber which comprises:
electrical conductor means;
means for connecting said electrical conductor means to a source of electrical energy;
insulating means encapsulating and electrically insulating said conductor means, said insulating means being of a material which is substantially inert in body fluids and tissue;
electrode means electrically connected to said electrical conductor means; and
a plurality of pliant non-conducting tine means extending from said insulating means for engaging body tissue, without penetration of the tissue, to urge said electrode means in a given, nominally transverse direction, none of said tine means extending in a direction less than 90° from said given direction.

12. The body implantable lead of claim 11 wherein said electrode means extends beyond said insulating means in at least said given direction.

13. The body implantable lead of claim 11 wherein said tine means are generally symmetrically arranged with respect to said given direction.

14. The body implantable lead of claim 13 wherein said tine means extend in substantially the same general direction from different locations on said insulating means.

15. The body implantable lead of claim 14 wherein said electrode means comprises conductive tip means including a portion skewed from the direction of said conductor means toward said given direction.

16. The body implantable lead of claim 11 wherein said electrode means comprises conductive tip means including a portion skewed from the direction of said conductor means toward said given direction.

17. The body implantable lead of claim 16 wherein said tine means extend in substantially the same general direction from different locations on said insulating means.

18. The transvenous lead of claim 11 wherein said insulating means has a preformed J configuration and a lumen adapted to accept a stylet.

19. The transvenous lead of claim 18 wherein the portion of said insulating means which forms said J configuration has a larger cross-sectional area than the remainder of said insulating means.

20. The body implantable lead of claim 19 wherein said electrode means extends beyond said insulating means in at least said given direction.

21. The body implantable lead of claim 20 wherein said tine means are generally symmetrically arranged with respect to said given direction.

22. The body implantable lead of claim 21 wherein said electrode means comprises conductive tip means including a portion skewed from the direction of said conductor means toward said given direction.

23. The body implantable lead of claim 22 wherein said tine means extend in substantially the same general direction from different locations on said insulating means.

* * * * *